US00PP32970P2

(12) United States Plant Patent
de Jong

(10) Patent No.: US PP32,970 P2
(45) Date of Patent: Apr. 13, 2021

(54) ***HYDRANGEA* PLANT NAMED 'MYSTERIOUS'**

(50) Latin Name: *Hydrangea macrophylla*
Varietal Denomination: Mysterious

(71) Applicant: Jos de Jong, Boskoop (NL)

(72) Inventor: Jos de Jong, Boskoop (NL)

(73) Assignee: DE JONG PLANT B.V., Boskoop (NL)

( * ) Notice: Subject to any disclaimer, the term of this patent is extended or adjusted under 35 U.S.C. 154(b) by 4 days.

(21) Appl. No.: 16/873,230

(22) Filed: Feb. 27, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea macrophylla* plant named 'Mysterious' that is characterized by its inflorescences that are flattened globular in shape with conspicuous sterile flowers, its strong branches, its sterile flower with sepal colors that range in different conditions from red-purple (non-bluing conditions) and violet-blue (bluing conditions), and its sterile flowers with sepals that have light to medium green blotches that vary in size and frequency (from no blotches to almost completely covered).

2 Drawing Sheets

Botanical classification: *Hydrangea macrophylla.*
Varietal denomination: 'Mysterious'.

BACKGROUND OF THE INVENTION

The present invention relates to a new and distinct cultivar of *Hydrangea macrophylla* and will be referred to hereafter by its cultivar name, 'Mysterious'. 'Mysterious' represents a new bigleaf *Hydrangea*, a perennial shrub grown for landscape use and as a potted plant.

'Mysterious' derived from an ongoing controlled breeding program directed by the Inventors. An objective of the breeding program included developing a new cultivar of *Hydrangea* with a floriferous blooming habit, improved plant shape, unique inflorescence coloration and other desirable traits.

'Mysterious' arose from a controlled cross made by the Inventor in Boskoop, The Netherlands in August of 2005 between unnamed and unpatented proprietary plants in the Inventor's breeding program. 'Mysterious' was selected as a single unique plant from amongst the resulting seedlings in summer of 2010.

Asexual propagation of the new cultivar was first accomplished by stem cuttings by the Inventor in May of 2011 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Mysterious' as a unique cultivar of *Hydrangea macrophylla.*

1. 'Mysterious' exhibits inflorescences that are flattened globular in shape with conspicuous sterile flowers.
2. 'Mysterious' exhibits strong branches.
3. 'Mysterious' exhibits sterile flower with sepal colors that range in different conditions from red-purple (non-bluing conditions) and violet-blue (bluing conditions).
4. 'Mysterious' exhibits sterile flowers with sepals that have light to medium green blotches that vary in size and frequency (from no blotches to almost completely covered).

The female parent of 'Mysterious' differs from 'Mysterious' in having a less compact plant habit and a more vigorous growth habit. The male parent of 'Mysterious' differs from 'Mysterious' in having a poorly branched and considerably less compact plant habit, a more vigorous growth habit, and sterile flower sepals that are red in color and lacks green colored blotches. 'Mysterious' can be most closely compared to the *Hydrangea macrophylla* cultivars 'AB Green Shadow' (not patented) and 'Hokomathyst' (U.S. Plant Pat. No. 22,261). 'AB Green Shadow' and 'Hokomathyst' are both similar to 'Mysterious' in having color blotching on the sepals of sterile flowers. 'AB Green Shadow' differs from 'Mysterious' in having sterile flowers that are darker and more red in color and changing to a darker red color during maturity and in not being suitable for growing under bluing conditions. 'Hokomathyst' differs from 'Mysterious' in having longer shoots, a more vigorous growth habit, and inflorescences that are larger in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Hydrangea*. The photographs were taken of two-year-old plants of 'Mysterious' as grown in a greenhouse in a 21-cm container in Boskoop, The Netherlands.

The photographs in FIG. 1 provides a side view of 'Mysterious' in bloom.

Figure 1:
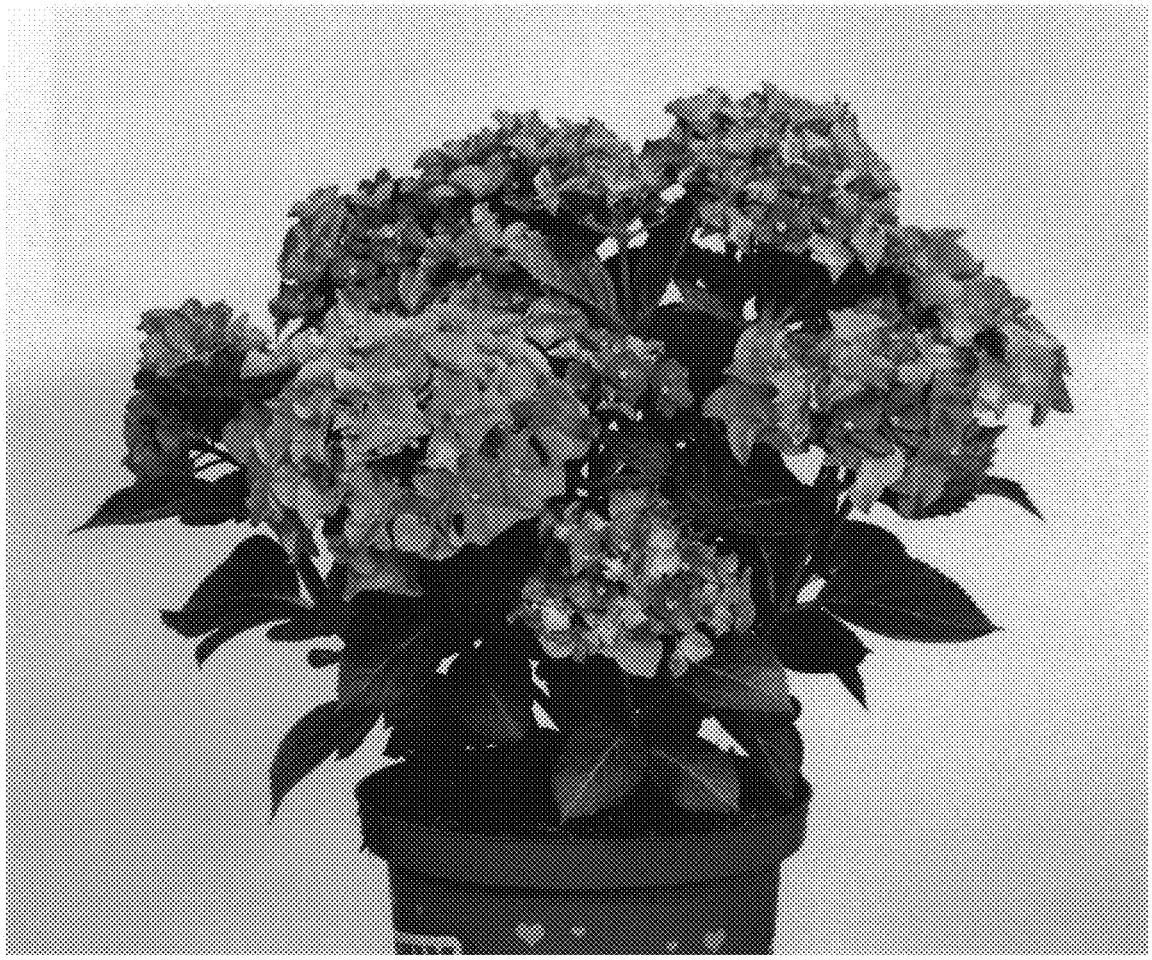
Figure 2:
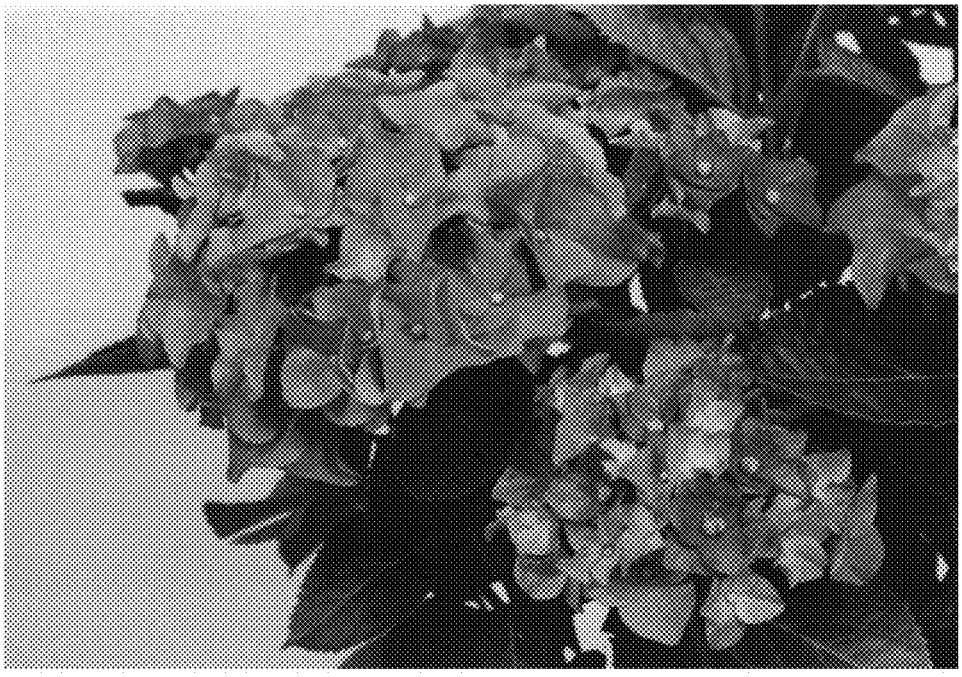

The photograph in FIG. 2 provides a close-up view of the inflorescence of 'Mysterious'.

Figure 3:
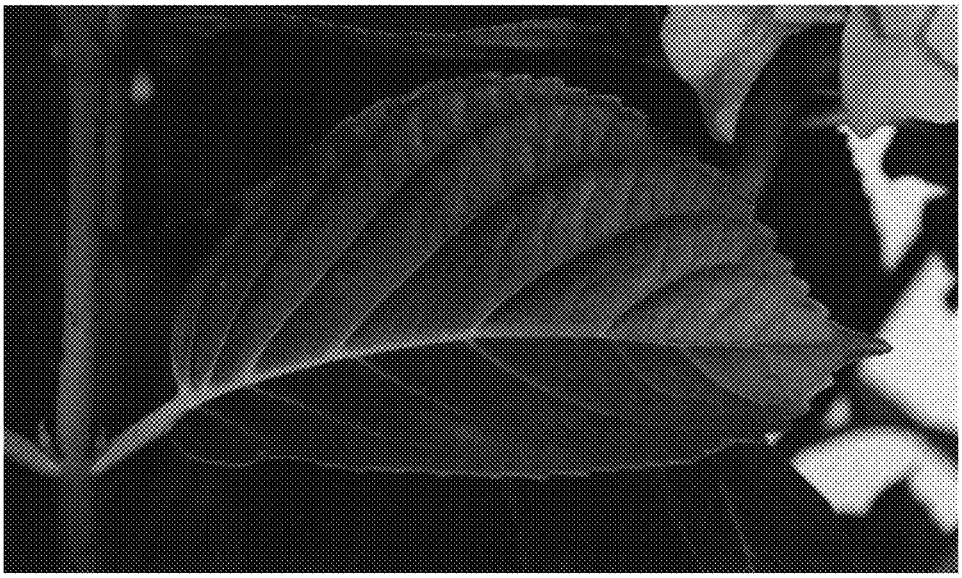

The photograph in FIG. 3 provides a close-up view of the foliage of 'Mysterious'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Mysterious' as grown in a greenhouse in 21-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Early summer to late summer in The Netherlands.

*Plant type*.—Deciduous shrub, mophead type *Hydrangea*.

*Plant habit*.—Broad spreading, upright, compact.

*Height and spread*.—An average of 35.8 cm in in height and 46 cm in spread.

*Hardiness*.—At least U.S.D.A. Zones 5 to 9.

*Diseases and pests*.—No susceptibility and resistance to diseases or pests has been observed.

*Root description*.—Fine and fibrous, 161C in color.

*Propagation*.—Stem cuttings.

*Root development*.—An average of 4 weeks for root initiation with a young rooted plant produced in an average of 18 weeks.

*Growth rate and vigor*.—Moderate.

Stem description:

*Stem shape*.—Rounded.

*Stem strength*.—Strong.

*Stem color*.—Young; 144A, mature between 144A and 146C, older bark N199B, N199C and N200B.

*Stem size*.—An average of 21.9 cm in length (excluding inflorescence) and 6.5 mm in diameter.

*Stem surface*.—Glabrous, moderately lenticellate, lenticels; an average of 1.75 mm in length and 0.75 mm in diameter, N186C in color.

*Stem aspect*.—Upright, held in an average angle of 55° to the soil, varying between 20° and 90°.

*Internode length*.—An average of 5.5 cm.

*Branching*.—Freely branching with an average of 18 lateral branches.

Foliage description:

*Leaf shape*.—Broad ovate.

*Leaf arrangement*.—Opposite.

*Leaf division*.—Simple.

*Leaf base*.—Obtuse.

*Leaf apex*.—Apiculate.

*Leaf margins*.—Coarsely serrate.

*Leaf venation*.—Pinnate, color; color upper surface 145A, lower surface 145C.

*Leaf size*.—An average of 8.6 cm in length and 7.1 cm in width.

*Leaf attachment*.—Petiolate.

*Leaf number*.—An average of 8 per lateral stem.

*Leaf surface*.—Both surfaces; glabrous and slightly rugose.

*Leaf color*.—Young foliage; upper surface 144A, lower surface between 144B and 146C, mature foliage; upper surface between 143A and 146A, lower surface 144A and 146C.

*Petioles*.—An average of 1.2 cm in length and 3.5 mm in diameter, upper and lower surface 144C in color, surface smooth and slightly glossy.

Inflorescence description:

*Inflorescence type*.—Terminal panicle, rounded mophead comprised of a sterile flowers.

*Lastingness of inflorescence*.—Sterile flowers; persistent for an average of 2 months.

*Inflorescence number*.—One per lateral stem.

*Inflorescence size*.—An average of 9.3 cm in height and 16 cm in diameter.

*Flower number*.—An average of 145 sterile flowers.

*Flower fragrance*.—None.

*Flower aspect*.—Upright to outward.

*Flower size*.—Sterile flowers; an average of 4.3 cm in diameter and 1.9 cm in depth.

*Flower type*.—Rotate.

*Flower buds*.—Sterile flowers; an average of 8 mm in length and 1.3 cm in diameter, cup shaped, 145C.

*Peduncles*.—Moderately strong, round in shape, an average of 5.7 cm in length and 3 mm in width, main peduncle held straight on top of the lateral branch, lateral peduncle held in an average angle of 35° to main peduncle, 144B in color, surface is matte and covered with a thin pubescence average of 0.5 mm in length and too small to measure color and moderately covered with lenticels an average of 1 mm in length, 0.5 mm in diameter, 187C in color.

*Pedicels*.—Sterile flowers; held primarily at an average angle of 45° to upright from peduncle, an average of 2.4 cm in length and 2 mm in diameter, moderately strong strength, color; 144C, moderately to strongly tinged 70C and 93D, dull and densely pubescent surface covered with thin pubescence an average of 0.5 mm in length and too small to measure color.

*Petals*.—Sterile flowers; an average of 4 (occasionally 5), rotate in arrangement, acute apex, cuneate base, entire margins, ovate in shape, strongly concave in aspect, average of 4.5 cm in length and 3 mm in width, both surfaces; smooth, glabrous and dull, color; when opening upper surface N77D, changing to 76C at the margins and base, when opening lower surface 76D, changing to 76A at the margins, when fully open upper surface N77D, changing to 76C at the margins and base, when fully open lower surface 76D, changing to 76A at the margins.

*Sepals*.—Sterile flowers; 5, occasionally 4 to 6, rotate arrangement, bluntly acute apex, broadly cuneate to truncate and cordate base, margins are coarsely and un-deeply crenate to serrate-crenate and coarsely undulate, sepal shape is deltoid to nearly rhomboidal and cordate, moderately carinate, an average of 2.7 cm in length and 3.1 cm in width, both surfaces glabrous and dull, main and secondary veins moderately covered with very short hairs 0.3 mm in length, too small to measure color, color; when opening upper surface varying between 73A to 73B, changing to 76C and N82C at the base, when opening lower surface N74D, changing to a range of 145D and N82C and 145D at the base, when fully open upper surface varying between 67B to 67D and N82A, mottled with 70B, fading to a blend of 63A and 61B, top 144A and 71A, when fully open lower surface 70C and N82C and 91A, fading to 144B, base a blend of 70B and 144B and 84A.

Reproductive organs:

*Gynoecium*.—Sterile flowers; pistil; 3, occasionally 2, average of 1 mm in length, stigma; club-shaped, N155A in color, style; 0.5 mm in length, 76C in color, ovary; NN155A in color.

*Androecium*.—Sterile flowers; an average of 8 stamens, filaments; an average of 3.5 mm in length and NN155D in color, anthers; broadly oblong in shape, an average of 1 mm in length and 145C in color, pollen; moderate in quantity and 157C in color.

*Fruit and seed*.—None observed.

It is claimed:

1. A new and distinct cultivar of *Hydrangea* plant named 'Mysterious' substantially as herein illustrated and described.

* * * * *